United States Patent [19]

Armstrong et al.

[11] Patent Number: 5,782,636
[45] Date of Patent: Jul. 21, 1998

[54] BONE CONTOURING TOOL

[75] Inventors: Peter S. Armstrong, San Diego; Brian C. Myers, Carlsbad, both of Calif.

[73] Assignee: Sulzer Calcitek Inc., Carlsbad, Calif.

[21] Appl. No.: 723,611

[22] Filed: Oct. 2, 1996

[51] Int. Cl.$^6$ .................................................. A61C 3/02
[52] U.S. Cl. ........................ 433/165; 433/173; 408/225; 408/209
[58] Field of Search ................................ 433/165, 166, 433/172, 173, 174, 175, 176, 215; 408/72 B, 85, 209, 225

[56] References Cited

U.S. PATENT DOCUMENTS

| | | |
|---|---|---|
| 1,123,730 | 1/1915 | Greenfield ............................ 433/165 |
| 1,200,921 | 10/1916 | Chester . |
| 1,333,388 | 3/1920 | Chester . |
| 1,827,511 | 10/1931 | Evans . |
| 3,058,218 | 10/1962 | Kleesattel et al. . |
| 4,229,169 | 10/1980 | Smith et al. . |
| 4,297,059 | 10/1981 | Miyanga ............................ 408/225 |
| 4,352,610 | 10/1982 | Yankovoy et al. ................. 433/209 X |
| 4,465,463 | 8/1984 | Hison Olde . |
| 4,741,651 | 5/1988 | Despres ............................ 408/209 |
| 5,201,656 | 4/1993 | Sicurelli, Jr. . |
| 5,254,005 | 10/1993 | Zuest .................................... 433/173 |

FOREIGN PATENT DOCUMENTS

| | | |
|---|---|---|
| 1021597 | 2/1953 | France . |
| 680464 | 8/1939 | Germany . |
| 1659037-A1 | 6/1991 | Russian Federation . |
| 10311 | of 1901 | United Kingdom . |

OTHER PUBLICATIONS

Implant Innovations, Inc. "Surgical Price List" w/drawing of Bone Profiler and Guide, May 1995.

Publication 1: Busch & Co., Bur Advertisement, Journal of the American Aug. 1968, vol. 77, No. 2, p. 415.

Publication 2: A.D., Reading's Specification, Jun. 1882, p. 2893.

Publication 3: Busch & Co., Bur Advertisement, Fig. 130.

Publiation 5: Nobelpharma AB, Special Products Catalog, 1994, p. 13.

*Primary Examiner*—Nicholas D. Lucchesi
*Attorney, Agent, or Firm*—Philip S. Lyren

[57] ABSTRACT

A bone contouring tool for removing bony tissue surrounding an implanted dental implant and having an elongated shank with a blade and a pilot pin disposed at one end. The pilot pin extends downwardly from the blade and provides guidance during removal of the bony tissue.

20 Claims, 5 Drawing Sheets

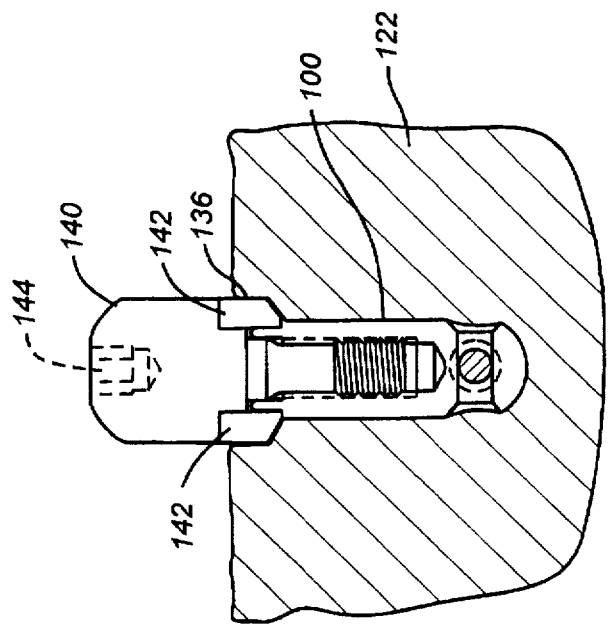
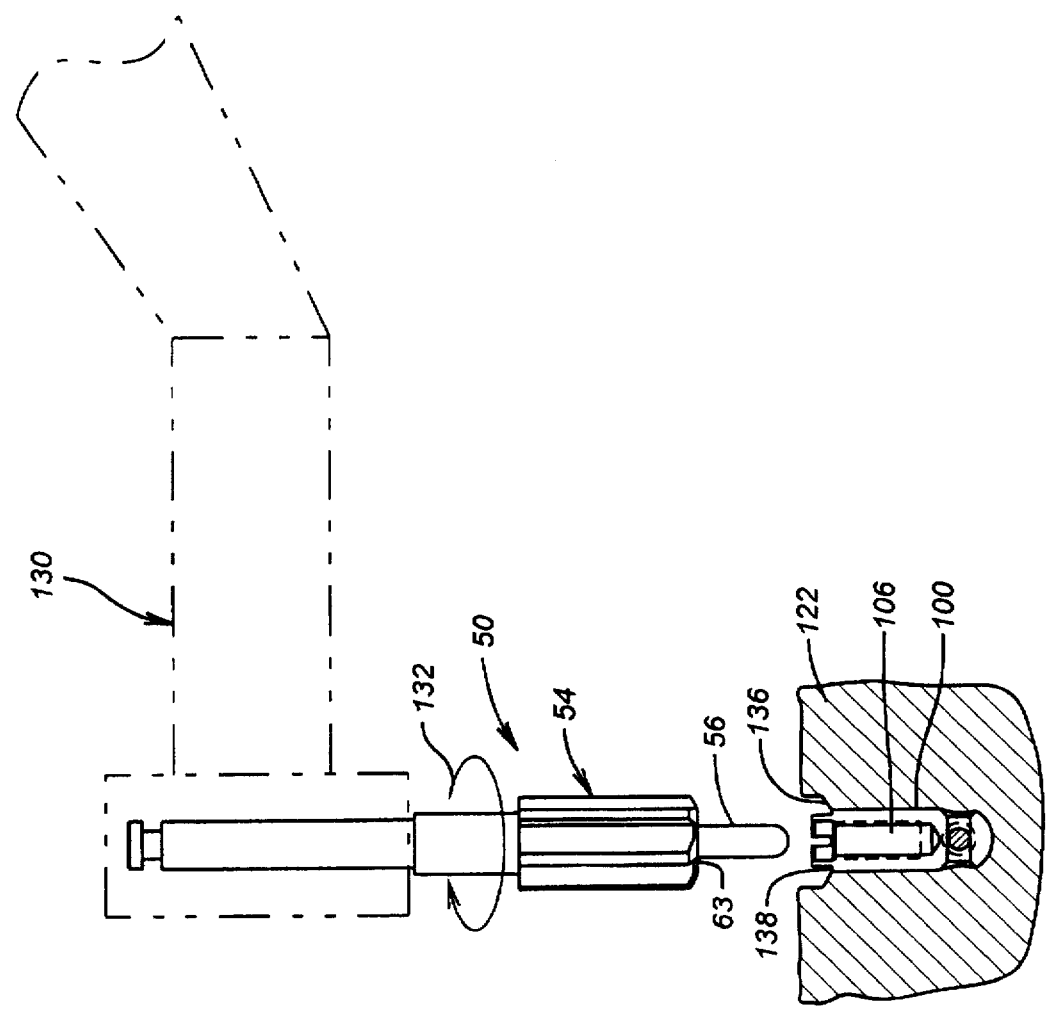

BONE CONTOURING TOOL

BACKGROUND OF THE INVENTION

Implantation of a dental implant typically requires two separate surgical procedures. During the first procedure, an incision is made along the gingival tissue at the implant site, and a cylindrical bore is drilled into the alveolar bone. Thereafter, an implant is affixed subcrestally in the bore and a healing screw is threaded into the coronal end of the implant. The tissue is sutured and the implant and the healing screw remain within the bone for several months as healing and osseointegration occur. During the second surgical procedure, the implant is re-exposed, and the healing screw is removed. Thereafter, an abutment is affixed to the implant, and a dental prosthesis is attached to the abutment.

One problem is that during the several months between the first and second surgical procedures, hard bony tissue forms around the coronal end of the implant. This tissue must be removed in order for the dental prosthesis to properly fit onto the implant. Some flared prosthesis, for example, contact the implant seating surface such that the flared portion gradually emerges from the gum line to portray a more natural appearance. The hard tissue prevents this type of contact.

Various dental bone cutting instruments, such as bone mills and bone profilers, are available to remove unwanted tissue surrounding the implant. FIG. 1 shows an example of one such prior art bone cutting instrument 10 to include a bone mill 12 and a guide 14. Bone mill 12 has a right-angle latchlock shank interface 16 at one end and tubular cutting feature 18 at an oppositely disposed second end. A cylindrical cavity 20 is disposed within the bone mill at the second end. Guide 14 has a cylindrical outer surface 22 and an extension 24.

As shown, implant 26 is imbedded within jaw bone 28 of a patient. An area 29 surrounding the implant represents the unwanted tissue that needs removal. In order to cut this tissue surrounding the implant, extension 24 of guide 14 screws into or otherwise engages with a cavity 30 within implant 26. Interface 16 connects to a motorized dental handpiece used to rotate bone mill 12. The second end of the bone mill then slides over top guide 14 such that surface 22 is disposed within cavity 20. The motorized handpiece turns the bone mill, and the cutting feature 18 cuts away the unwanted bone and tissue surrounding the implant.

One major disadvantage associated with many prior bone cutting instruments is that two separate components are required, namely a bone mill or profiler and a separate guide. It is desirable, however, to minimize the overall number of components and the handling of these components. The surgeon or clinician may, for example, drop the guide. If the guide is dropped outside the oral cavity, it may become lost or contaminated; and if it is dropped inside the oral cavity, it may be swallowed or aspirated.

Additionally, elimination of the separate guide would reduce the number of components manufactured for bone cutting. As such, the overall manufacturing and packaging cost for a bone cutting instrument would be decreased.

As another disadvantage, a separate bone mill and guide require the surgeon to perform more surgical steps during the prosthodontic implant operation. Any additional or unnecessary step make the surgical procedure more lengthy and cumbersome and ultimately increase the risk and trauma to the patient. In the prior art for example, separate steps are required to properly position the guide on the implant and then position the mill over the guide. Separate steps must then be used to remove the mill and the guide.

As a further disadvantage, once the implant is correctly positioned within the jawbone, movement and disturbance to the implant should be minimal. If a separate bone mill and guide are employed, incidental contact from the rotating bone mill may cause the guide to seize on the implant and disturb its position.

Additionally, contact between the rotating bone mill and guide may damage the guide. Such contact could also make removal of the guide from the implant difficult.

As yet another disadvantage, if the guide is not fully seated on the implant, the bone mill will bottom out before fully cutting to its capable depth. As such, the proper amount of unwanted tissue will not be cut.

As noted, various bone cutting instruments are available. Some of these instruments include rotary burrs, curettes, rongeurs, and the like. One problem with these instruments is the user is required to manually maneuver the cutting edge around the implant to remove the unwanted tissue. Such manual methods typically require the user to either remove more bone than necessary or remove small amounts of bone by trial and error until the dental prosthesis is properly seated. Manual methods of bone removal also increases the risk of inadvertently damaging the implant seating surface.

A significant need exists, therefore, for a device that does not exhibit the shortcomings of prior art dental bone cutting instruments. The present invention fulfills these needs and provides further advantages.

SUMMARY OF THE INVENTION

The present invention is directed toward a bone contouring tool for use in prosthodontic procedures and in particular for removing bony tissue surrounding an implanted dental implant. The bone contouring tool has an elongated shank with a blade formed at one end. The blade includes a plurality of cutting edges for cutting and removing the bony tissue. A pilot pin extends outwardly from the end adjacent the blade and has an elongated cylindrical configuration. The pilot pin is insertable into the implanted implant and provides guidance to the blade during bone removal.

One important advantage is the bone contouring tool of the present invention is formed as a single unit or component. A separate bone mill and guide are not needed. In this regard, a single piece bone contouring tool includes both a blade for cutting the bony tissue and a pilot pin for guiding the blade and maintaining it around the implant during cutting operations. Since a separate guide does not exist, there is no risk of dropping a guide during the dental procedure.

As another advantage, the number of steps required to remove bony tissue surrounding the implant are minimized. In this regard, separate steps are not required to position and then remove both a separate bone mill and guide. Rather, a single step of positioning the pilot pin within the implant simultaneously positions the blade at the correct cutting location around the implant. Additionally, removal of the pilot pin simultaneously removes the blade.

Additionally, movement and disturbance of the implant is minimal during cutting operations. The pilot pin has a smooth outer surface and extends downwardly along a vertical axis adjacent the blade. Additionally, in one embodiment, a cavity exists between the pilot pin and blade. This cavity receives the coronal portion of the implant and ensures stability and minimizes lateral movement of the bone contouring tool. Further, incidental contact from the rotating blade and implant is minimized or non-existent.

As a further advantage, the bone contouring tool provides a safeguard so the blade is not capable of cutting too deeply around the implant. The bottom surface of the blade contacts a seated surface on the implant and limits the distance the pilot pin engages the implant and thus the depth of cut around the implant.

The invention, accordingly, comprises the apparatus and method possessing the construction, combination of elements, and arrangement of parts which are exemplified in the following detailed description. For a fuller understanding of the nature and objects of the invention, reference should be made to the following detailed description taken in connection with the accompanying drawings.

BRIEF DESCRIPTION OF THE DRAWINGS

FIG. 7 illustrates a second stage during a surgical procedure utilizing the bone contouring tool; and FIG. 8 illustrates a third stage during a surgical procedure utilizing the bone contouring tool.

DETAILED DESCRIPTION OF THE PREFERRED EMBODIMENTS

Figure 1:
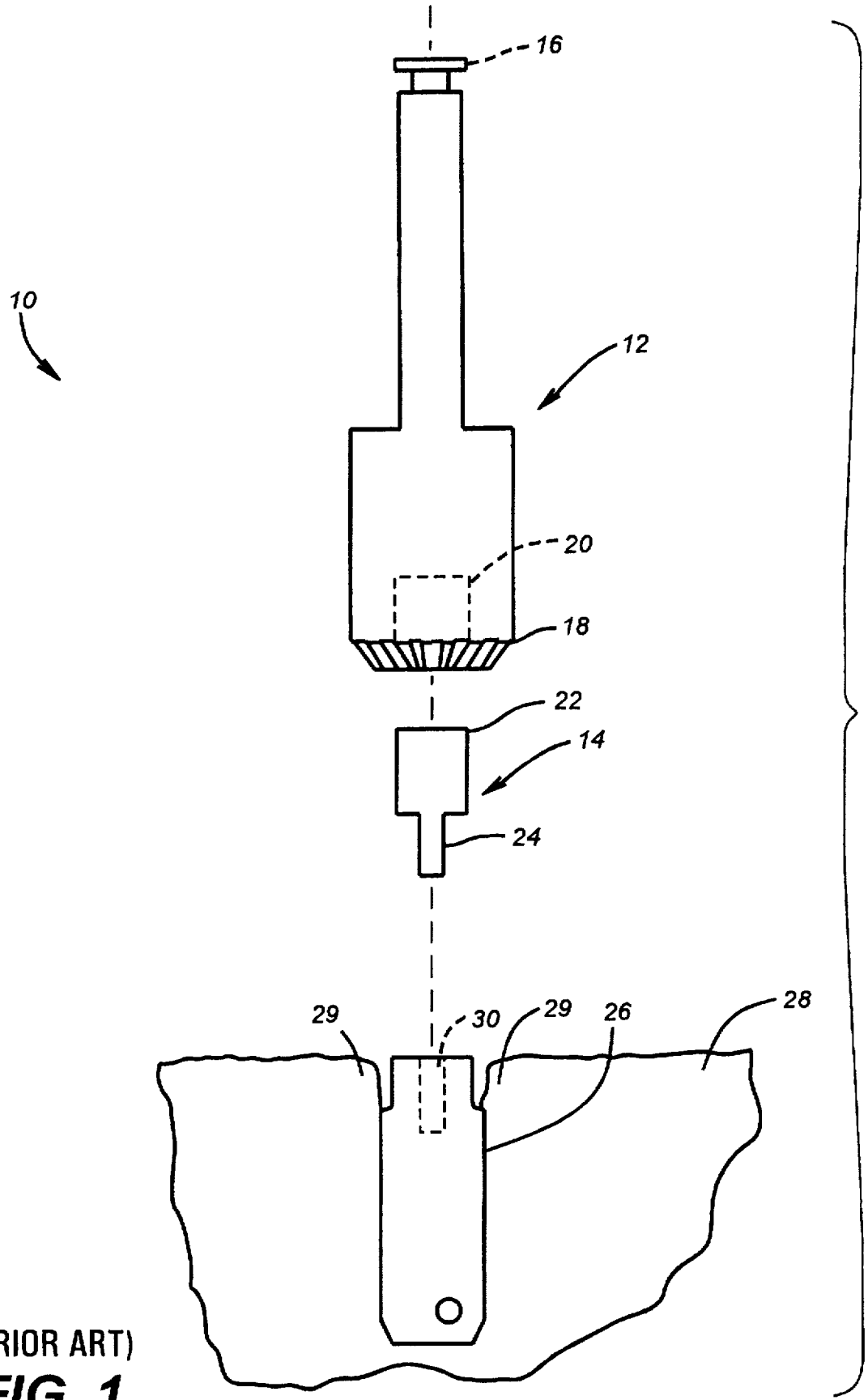
FIG. 1 illustrates a prior art cutting instrument positioned above an implanted dental implant.
Figure 2:
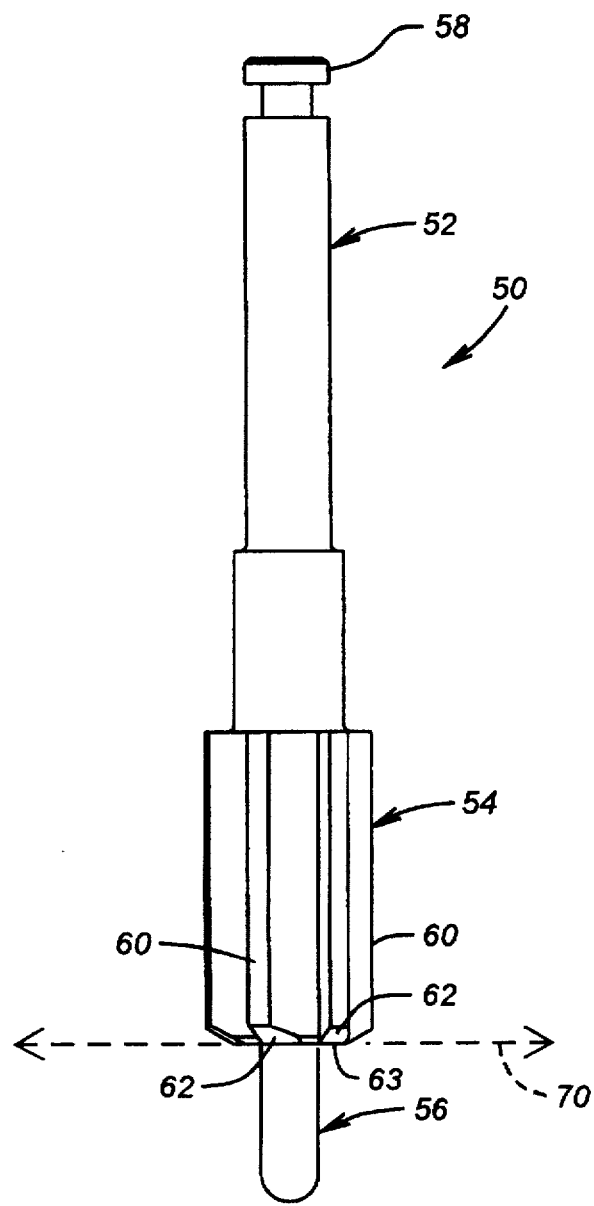
FIG. 2 is a bone contouring tool according to the present invention.

FIG. 2 shows a bone contouring tool 50 for use in dentistry and dental implant procedures. Tool 50 generally comprises a shank 52, a blade 54, and a pilot pin 56. One end of shank 52 has a standard right-angle latchlock interface 58 for connecting to a dental handpiece (not shown). Another end of shank 52 connects to blade 54.

In the preferred embodiment, blade 54 includes a plurality of flutes 60 each having a cutting edge or surface 62. These cutting surfaces 62 extend to an end surface 63 and are flared or canted with respect to a horizontal plane shown along dashed line 70. The angle of this cant and size of cutting surface 62 may vary depending on various factors, such as the width and depth of cut sought. Additionally, the configuration of flutes 60 and cutting surface 62 allows for bone chips to be cleared away from the implant site during cutting operation. Removal of bone chips away from the implant site helps provide the surgeon with an unobstructed view during cutting of tissue and also helps to minimize unwanted heat generation, such as heat generated at the implant site by the motorized dental handpiece. It will be appreciated that cutting surface 62 may have any one of various sizes and configurations adaptable for use in dentistry and known to those skilled in the art.

Figure 3:
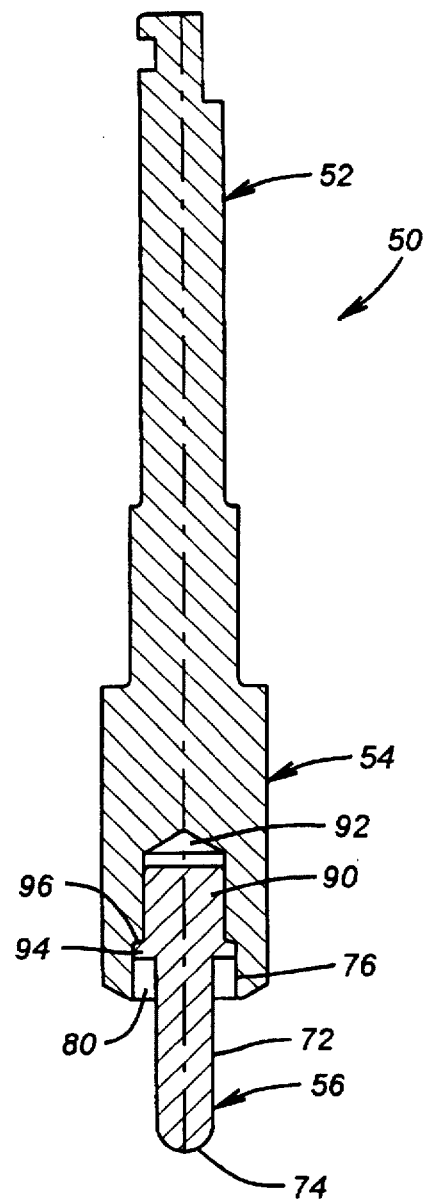
FIG. 3 is a cross section of the bone contouring tool of FIG. 2.

As shown in FIGS. 2 and 3, pilot pin 56 extends outwardly from an area adjacent blade 54. Preferably, pilot pin 56 has a generally elongated cylindrical configuration and has a smooth outer surface 72 and a rounded end 74. Outer surface 72 of pilot pin 56 and an inner surface 76 of blade 54 are separated apart to form a cavity 80 for receiving the coronal end of an implant (not shown).

As shown in FIG. 3, pilot pin 56 has a head portion 90 adapted to securely and permanently fit within a cavity 92. Head portion 90 includes a ridge 94 that abuts against a lip 96 formed on the interior surface of cavity 92. Pilot pin 56 must be firm and secure in order to form part of the bone contouring tool. The pilot pin may be manufactured as a separate component as shown in FIG. 3 or, alternatively, integrally formed as part of the bone contouring tool. Additionally, the pilot pin may have other configurations in order to engage the various types of dental implants known to those skilled in the art.

Figure 4B:
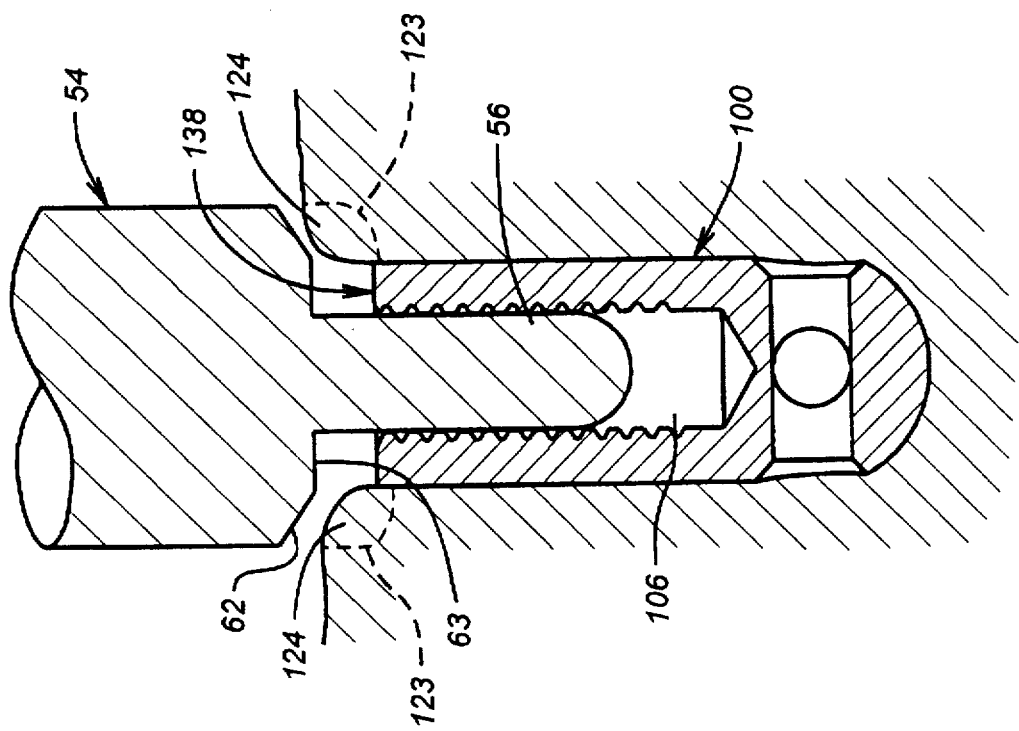
FIG. 4B is an alternate embodiment of an enlarged sectional view of a bone contouring tool engaging an implant.
Figure 4A:
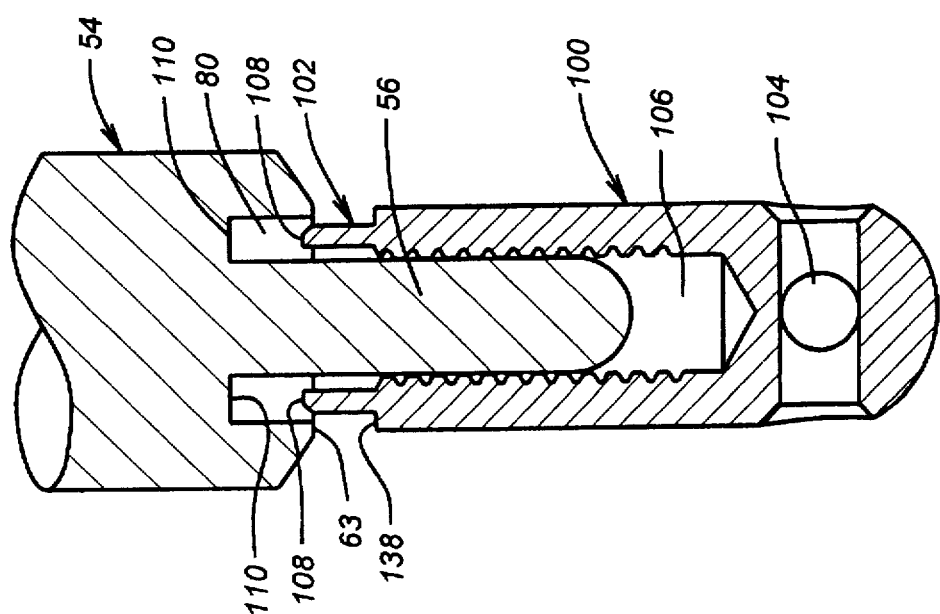
FIG. 4A is an enlarged sectional view of a bone contouring tool engaging an implant.

Turning now to FIG. 4A, pilot pin 56 is configured to be removably engageable with an implant 100. In this regard, implant 100 may be any one of various implants known to those skilled in the art. For illustration purposes, implant 100 includes a coronal or top portion 102, a bore 104 to aid osseointegration, and an inner chamber 106 to receive a healing screw (not shown).

As shown, pilot pin 56 fits within chamber 106 and is shaped to freely rotate therein. Coronal portion 102 extends within cavity 80 until end 63 abuts against surface 138. Engagement between pilot pin 56 and cavity 80 stabilize the bone contouring tool during cutting operations. It will appreciated that the bone contouring tool may be dimensioned to interface with various implant ends, such as spline, external hex, internal polygon or other interfaces.

FIG. 4B shows an alternate embodiment to the bone contouring tool of FIG. 4A. The main difference between these two figures is the bone contouring tool of FIG. 4B does not include a cavity (shown as cavity 80 in FIG. 4A). Such a cavity is not necessary with many types of implants, such as implants having an internal anti-rotational feature or implants not having any type of anti-rotational feature.

In FIG. 4B, pilot pin 56 extends within chamber 106 until end 63 abuts against surface 138. Cutting surface 62 is positioned over the jaw bone and ready to remove hard bony tissue 124 formed around the implant. Dashed line 123 outlines the bony tissue to be removed. Removal of this tissue is more fully discussed in connection with FIGS. 6–8.

Figure 5:
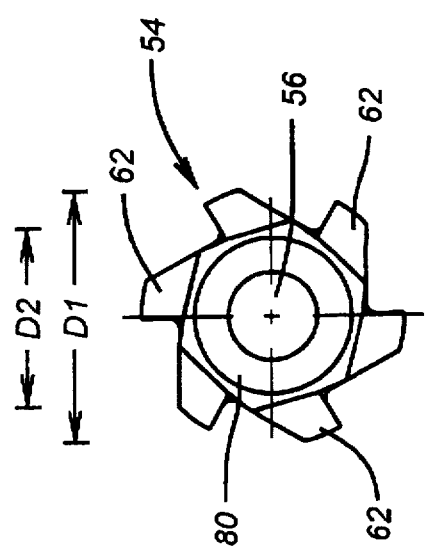
FIG. 5 is a bottom view of the bone contouring tool of FIG. 2.

FIG. 5 illustrates a bottom view of the bone contouring tool and shows blade 54 in more detail. A plurality of cutting surfaces 62 are circumferentially disposed about the end of blade 54 and form around pilot pin 56. Cutting surfaces 62 may have various geometric configurations or designs to cut bone or tissue formed around the coronal end of an implanted dental implant. Cutting surfaces 62 have an outer diameter D1 and an inner diameter D2. Diameter D1 may be varied to accommodate various prosthetic diameters, and diameter D2 may be varied to accommodate various implant diameters. Additionally, as shown, pilot pin 56 is centrally located with respect to cutting surfaces 62.

Figure 6:
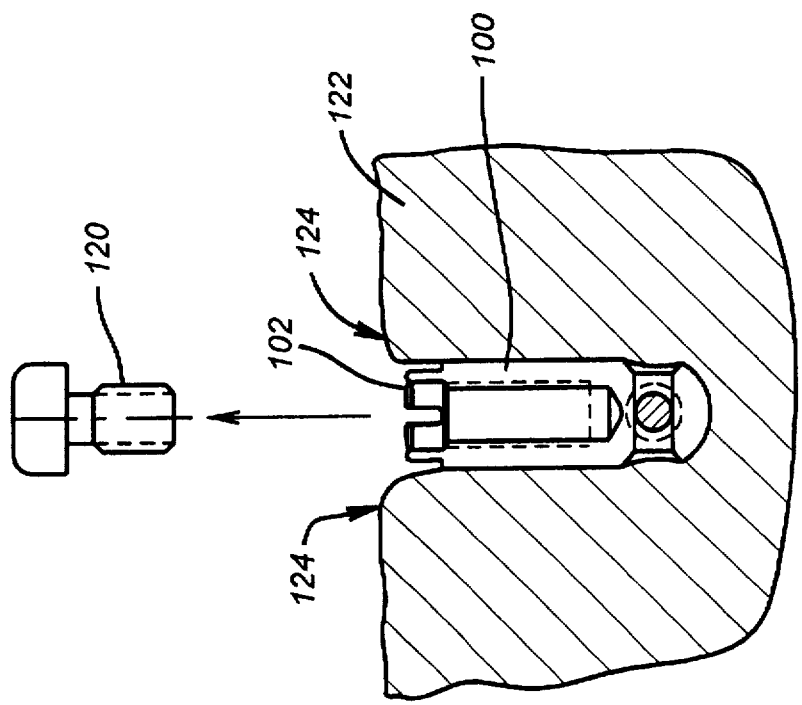
FIG. 6 illustrates a first stage during a surgical procedure utilizing the bone contouring tool.

FIGS. 6–8 illustrate a method for using the bone contouring tool of the present invention. FIG. 6 shows implant 100 implanted within jaw bone 122 of a patient. The implant may be implanted using procedures known to those skilled in the art. During a typical implant procedure, an incision is made along the gingival tissue at the implant site, and a cylindrical bore is drilled into the alveolar bone. Thereafter, the implant is affixed subcrestally in the bore and a healing screw 120 is threaded into the coronal end of the implant. The tissue is sutured and the implant and the healing screw remain within the bone for several months as healing and osseointegration occur. During the second surgical procedure, the implant is re-exposed, and the healing screw is removed. Thereafter, an abutment is affixed to the implant, and a dental prosthesis is attached to the abutment.

FIG. 6 illustrates the second phase of the surgical procedure and shows a healing screw 120 being removed from implant 100 within a jaw bone 122 of a patient. During the several months between the first and second surgical procedures, hard bony tissue 124 forms around coronal end 102 of implant 100. This tissue 124 obstructs a proper fit or seating between the implant and some abutments or dental prosthesis. As such, tissue 124 must be removed.

FIG. 7 shows bone contouring tool 50 connected to a motorized dental handpiece 130 (shown with dashed lines). Handpiece 130 provides power to rotate bone contouring tool 50 in a clockwise direction as indicated by line 132. The bone contouring tool is positioned above the implant site and is lowered to implant 100 such that pilot pin 56 engages within chamber 106. As shown in FIGS. 4A and 4B, pilot pin 56 extends into chamber 106 and is freely rotatable therein. In this position, pilot pin 56 stabilizes the bone contouring tool and provides a guide for ensuring straight and accurate vertical displacement of blade 54 with little lateral movement. Minimal lateral movement also ensures that rotation of the blade will not damage the implant and in particular the coronal end.

As pilot pin 56 descends into chamber 106, cutting surface 62 of blade 54 cuts and removes tissue 124. As best shown in FIG. 7, a uniform circular clearance or path 136 is cut around coronal end 102. Clearance 136 may have various widths depending on the size and configuration of blade 54 and cutting surface 62 selected. In order to achieve a larger clearance, for example, the surgeon may select a bone contouring tool having a larger blade diameter. Additionally, clearance 136 may be cut to have various depths depending on the application at hand. In order to achieve a deeper cut, for example, pilot pin 56 would be more deeply engaged into chamber 106. The surgeon or clinician, however, is prevented from cutting too deeply. In this regard, looking to FIGS. 4A, 4B, and 7, implant 100 has a seating surface 138 that will abut with end 63 of blade 54. This abutment prevents pilot pin 56 from engaging too deeply into chamber 106 and thus cutting clearance 136 too deeply.

The pilot pin may be prevented from engaging to deeply using alternative methods as well. For example, looking to FIGS. 4A and 4B, surface 110 may provide a backstop for end 108 of implant 100. As such, pilot pin 56 can be engaged within chamber 106 until end 108 contacts surface 110. The length of cavity 80 may be varied to change the distance pilot pin 56 extends within chamber 106.

After the appropriate amount of bony tissue is removed, an abutment or prosthetic may be attached to the implant. FIG. 8 shows one such abutment or prosthetic 140 connected to implant 100. Abutment 140 has a cylindrical end portion 142 that fits within clearance 136 in order to provide proper fit and seating with implant 100. End 142 should fit snugly and minimize or eliminate any gaps with jaw bone 122. A cavity 144 is provided within the top of abutment 140 for securing the abutment to the implant with a hex wrench (not shown).

Since certain changes may be made in the above-described apparatus and method without departing from the scope of the invention herein involved, all matter contained in the description or shown in the accompanying drawings shall be interpreted as illustrative and not in a limiting sense.

The invention claimed is:

1. A one piece bone contouring tool for removing tissue surrounding a dental implant, comprising:

an elongated shank;

blade means connected to said shank for removing bone tissue surrounding said implant: and a pilot pin connected to and extending downwardly from said blade means.

2. The bone contouring tool of claim 1 in which said pilot pin is insertable into said implant and has an elongated cylindrical configuration with a smooth outer surface for providing rotational engagement with said implant.

3. The bone contouring tool of claim 1 in which said pilot pin is insertable into said implant to guide said blade means around the perimeter of said implant during removal of said tissue.

4. The bone contouring tool of claim 1 in which said blade means includes a plurality of cutting edges circumferentially disposed around said pilot pin.

5. The bone contouring tool of claim 1 in which:

said blade means extends around said pilot pin; and a cavity extends between said pilot pin and said blade means for receiving said implant.

6. The bone contouring tool of claim 5 in which:

a surface defines a top portion of said cavity; and said pilot pin is insertable into said implant until said implant abuts said surface.

7. The bone contouring tool of claim 1 in which:

said blade means includes a bottom surface; and said pilot pin is insertable into said implant until said implant abuts said bottom surface.

8. The bone contouring tool of claim 1 in which:

said blade means is canted to remove bone chips away from around said implant; and said pilot pin has a smooth and non-cutting outer surface.

9. A method for removing bony tissue surrounding an implanted dental implant, comprising the steps of:

providing a bone contouring tool having a shank a blade connected to said shank, and a pilot pin connected to and extending downwardly from one end of said shank;

connecting another end of said shank to a motorized dental handpiece;

inserting said pilot pin into a cavity extending within said implant;

rotating said bone contouring tool with said handpiece;

cutting said bony tissue with said blade; and removing sa id pilot pin from said cavity.

10. The method of claim 9 further comprising the step of cutting said bony tissue until said bone contouring tool abuts against said implant.

11. The method of claim 9 further comprising the step of guiding said blade onto said bony tissue using said pilot pin.

12. The method of claim 9 further comprising the step of:

positioning said blade around said implant; and guiding said blade through said bony tissue during said step of cutting said bony tissue.

13. The method of claim 9 further comprising the steps of:

providing said blade with canted cutting edges; and removing bone chips away from said bony tissue surrounding said implant with said cutting edges.

14. A one piece tool for removing bony tissue around an implanted dental implant, said tool comprising:

a shank portion;

a blade connected to said shank portion and having a plurality of cutting edges for cutting said bony tissue; and a pilot pin extending outwardly from one end of said shank portion and having a non-cutting outer surface insertable into said implant for providing rotational engagement with said implant.

15. The tool of claim 14 in which said pilot pin is insertable within said implant for guiding said cutting edges onto said bony tissue.

16. The tool of claim 14 in which said shank portion, said blade, and said pilot pin are integrally formed.

17. The tool of claim 14 in which said cutting edges remove a uniform, circumferential section of said bony tissue from around said implant.

18. The tool of claim 14 in which said pilot pin guides said cutting edges through said bony tissue until said tool contacts said implant.

19. The tool of claim 14 in which said cutting edges are canted to remove bone chips away from an area around said implant.

20. The tool of claim 14 in which:

said pilot pin has an elongated cylindrical configuration; and said cutting edges form around said pilot pin.

* * * * *